United States Patent [19]

Ballies

[11] Patent Number: 5,037,549
[45] Date of Patent: Aug. 6, 1991

[54] DEVICE FOR THE REMOVAL OF SERUM SEPARATED FROM BLOOD

[76] Inventor: Uwe Ballies, Jagersberg 7-9, 2300 Kiel, Fed. Rep. of Germany

[21] Appl. No.: 466,272

[22] PCT Filed: Jun. 23, 1989

[86] PCT No.: PCT/DE89/00413
§ 371 Date: Apr. 23, 1990
§ 102(e) Date: Apr. 23, 1990

[87] PCT Pub. No.: WO89/12812
PCT Pub. Date: Dec. 28, 1989

[30] Foreign Application Priority Data

Jun. 24, 1988 [DE] Fed. Rep. of Germany ... 8808138[U]

[51] Int. Cl.$^5$ ............................................... B01D 21/26
[52] U.S. Cl. ..................................... 210/515; 210/514; 210/518; 422/101; 422/102; 494/16
[58] Field of Search ...................... 494/16-20; 210/513, 514, 515, 516, 518, 359; 422/101, 102

[56] References Cited

U.S. PATENT DOCUMENTS

| | | |
|---|---|---|
| 3,850,174 | 11/1974 | Ayres .................................. 210/513 |
| 3,865,731 | 2/1975 | Seitz .................................... 210/359 |
| 4,046,699 | 9/1977 | Zine, Jr. .............................. 210/516 |
| 4,052,320 | 10/1977 | Jakubowicz ........................ 210/516 |
| 4,154,690 | 5/1979 | Ballies ................................. 210/516 |
| 4,472,180 | 9/1984 | Montefiori ......................... 210/513 |
| 4,602,995 | 7/1986 | Cassaday et al. ................... 210/515 |
| 4,891,134 | 1/1990 | Vcelka ................................ 210/518 |
| 4,957,637 | 9/1990 | Cornell ............................... 210/516 |

FOREIGN PATENT DOCUMENTS 2383710 10/1978 France .

Primary Examiner—W. Gary Jones
Attorney, Agent, or Firm—Herbert W. Larson

[57] ABSTRACT

A test tube is closed with a plug having a cannula piercing the center of the plug. A first collar surrounds the plug and a second collar above the first collar extends away from the plug and receives a tightly fitted serum container. The serum container is separated from a top opening to the cannula by a first air space. A second air space exists between a bottom of the plug and a top layer of a blood sample. A channel along an inner edge of the second collar allows serum to move upwards into the serum container during a centrifuge process by virtue of increased air pressure within the test tube caused by the serum container pressing on the first air space.

4 Claims, 1 Drawing Sheet

DEVICE FOR THE REMOVAL OF SERUM SEPARATED FROM BLOOD

BACKGROUND OF THE INVENTION

This invention relates to blood separation devices. More particularly, the invention concerns a device for the removal of the serum which is separated from the blood cake through centrifugation of a test tube, closed at least on one side by a plug, the device comprising a top which is essentially rotationally symmetrical and which is furnished with a first collar encircling the plug and a cannula which penetrates the plug, and comprising a serum container for receiving the part of the serum which settles during centrifugation in the test tube.

A test tube for receiving a blood sample which is to be separated through centrifugation is known from DE-OS 27 11 336. This test tube receives a separating body, the specific gravity of which is between those of the two components of the blood to be separated. The separating body moves during centrifugation between the two components and separates the components after completion of the centrifugation by blocking the diameter of the separation tube. This test-tube construction is easy to handle. It may be felt to be a disadvantage that the sample container in this system is not closed.

In addition, a device is known which removes the serum of a blood sample to be separated through centrifugation into blood cake and serum with the prior art features of claim 1. For transferring the serum into a special serum container the rubber plug is penetrated by a cannula which is set on a top which is to be pushed onto the rubber plug. A sucking tube which is attached to a serum container is introduced into the cannula which penetrates the rubber plug. Serum is now pumped by means of a special vacuum pump from the test tube into the serum container.

This system has the disadvantage that the serum has to be pumped by a special pump from the test tube into the serum container after centrifugation.

SUMMARY OF THE INVENTION

It is the object of the invention to provide a device described above in which the serum is transferred automatically into the separated serum container after centrifugation.

In accordance with the invention this object is solved in that the top is provided with a second collar which extends away from the plug. This collar receives the serum container in a piston-like gliding motion. The cannula extends down into the serum and the second collar or the serum container is provided with a passage which runs from the cannula to the serum container. The passage is opened only when the serum container is lowered to the plug.

A preferred embodiment is characterized in that the passage is formed as a groove extending along the inner wall of the second collar above the upper edge of the serum container when the serum container is lowered to the plug.

Furthermore, it is suggested that the passage is so formed that it holds back fibers.

Furthermore, a cap closing the serum container may be provided.

BRIEF DESCRIPTION OF THE DRAWINGS

The invention is now explained by means of a drawing, in which.

DETAILED DESCRIPTION OF THE INVENTION

Figures 1, 2:
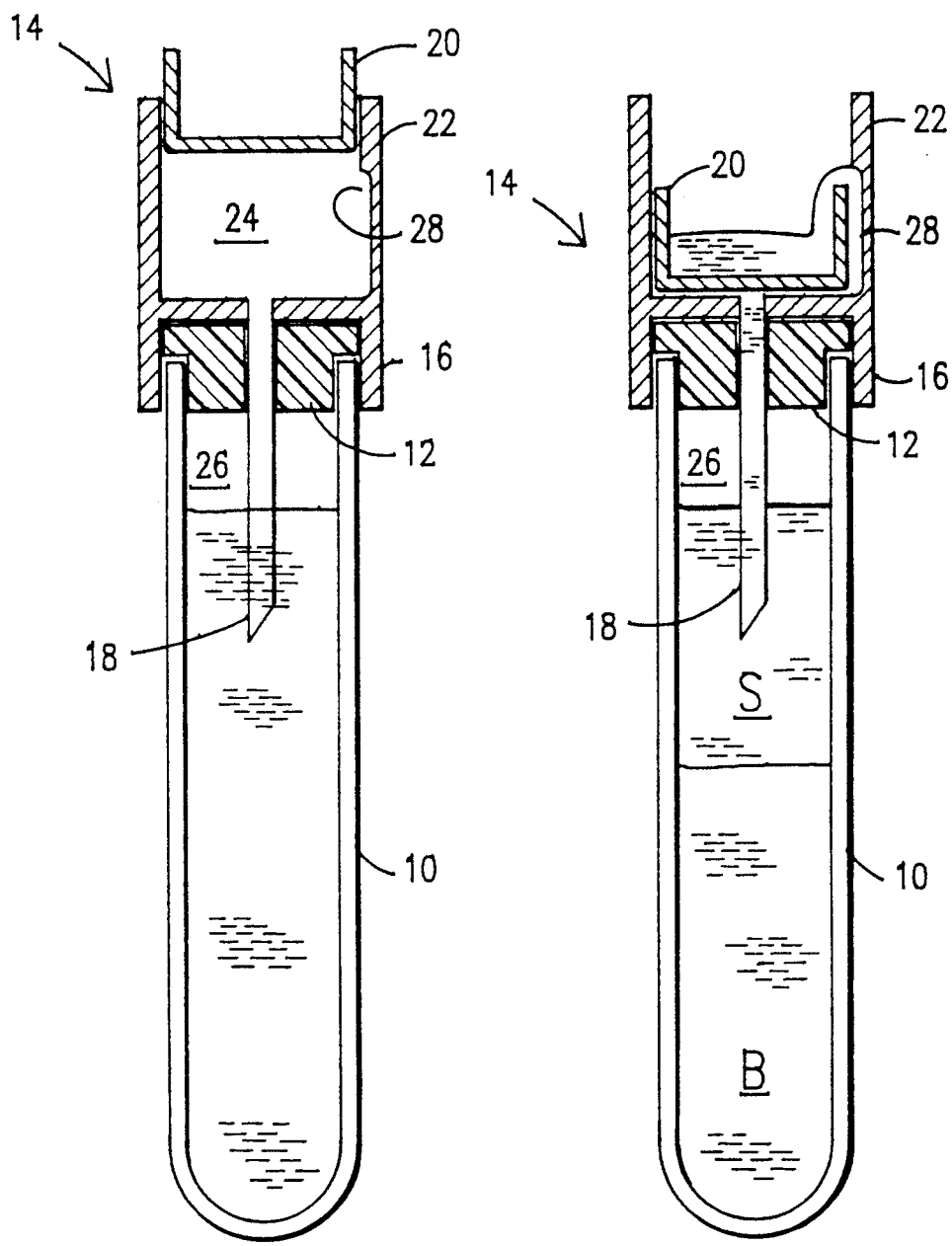
FIG. 1 shows a section-view through a test tube of the invention after attaching the top, but before centrifugation.
FIG. 2 shows a view in accordance with FIG. 1, but after centrifugation.

The test tube 10, is closed by a plug 12. Attached to the plug 12 is a top 14 which comprises a first collar 16 encircling the plug 12, a cannula 18 penetrating the plug 12 and a second collar 22 extending away from the plug 12. The second collar 22 receives a serum container 20 in a piston-like gliding motion. Before centrifugation the serum container 20 is placed at such a distance from the rubber plug 12 that space 24 is formed between the serum container 20 and the rubber plug 12 (FIG. 1). During centrifugation the serum container 20 is lowered because of the centrifugal force in the direction of the rubber plug 12. Due to the fact that the serum container 20 acts as a seal at the inner wall of the second collar 22 the air in the space 24 is displaced by the serum container 20. The air in the space 24 is pressed through the cannula 18 which penetrates the rubber plug 12 into the test tube 10. As a result, higher pressure is created in the test tube. This high pressure in the test tube 10, causes the serum S, which collects at the top, to rise above the level of the serum outside of the cannula 18. A further rise is added by the centrifugal force. During centrifugation the centrifugal force, presses the fluid column in the cannula 18 outwards; i.e., to the closed end of the test tube 10, and acts against the pressure exerted from the air in the space 26 in the test tube over the serum. After the end of centrifugation, however, the air under pressure in the space 26 encircling the cannula 18 causes a transfer of the serum through the cannula 18. This causes the collected serum to move upward through the rubber plug 12. Passage 28 which is formed in the shown embodiment as a groove in the wall of the second collar 22 of the top 14 extends parallel to the axis just above the upper edge of the serum container 22. The passage 28 provides a connection between the cannula 18 and the serum container 20 only when the serum container 20 is lowered. It allows the serum which is forced out from the test tube 10 to enter into the serum container 20 which is received from the second collar 22. The serum is now received by the separated serum container 20. The test tube can be set into an analyzer without a special step of transferring the serum into a special serum container.

It is obvious that the thickness of the cannula is to be chosen so that the effects of high pressure result. The cannula might, as an alternate from the shown embodiment be attached at the body of the serum container 20, if the cannula 18 is provided in the area of the bottom of the serum container 20 with a cut out which allows a displacing of the air in the space 24 through the cannula into the test container. This would cause a raising of the serum through the cannula 18 beneath the body of the serum container 20 through the passage 28 into the serum container 20 during lowering of the serum container.

The forming of the passage 28 so that fibers or the like are held back may be caused by suitable roughness or the structure of the body of the serum container 20 or the upper surface of the top attached to the plug which causes the fibers to be held back. The inventive basic idea is to provide a test tube in which different from the state of the art, the serum is not to be pumped out from the test tube in a special step but is forced automatically after the end of the centrifugation by means of a high pressure build up during centrifugation into the special serum container. This basic idea may be realized in different ways. Especially, different formations of the passage through which the serum is transferred through the cannula into the serum container are possible. It is important that the passage is provided so that a communication between the space between the body of the serum container and the rubber plug is only present when the serum container is more or less completely lowered during centrifugation.

I claim:

1. A device for the removal of a serum which is separated from a blood cake through centrifugation of a test tube, closed at least on one side by a plug having a lower annular portion in contact with an inner top wall of the test tube, the device comprising a top essentially rotationally symmetrical and furnished with a first annular collar enclosing an outer top wall of the test tube together with the plug and a cannula integral with a lower portion of the top penetrating the plug, a serum container for receiving a part of the serum separated during centrifugation in the test tube, the top provided with a second annular collar extending away from the first collar and receiving the serum container in a tight piston-like fit, an inner lower wall portion of the second collar providing a passage together with an outer wall of the serum container from the cannula to an interior of the serum container, the passage opening to allow serum to flow only when the serum container is lowered to the plug.

2. A device in accordance with claim 1, wherein the passage is formed as a groove along the inner lower wall portion of the second collar and is located at least partially above an upper edge of the serum container when the serum container is lowered to the plug.

3. A device in accordance with claim 1 or 2, wherein the passage is so formed that it holds back fibers.

4. A device in accordance with claim 1 or 2, wherein a cap closes the serum container.

* * * * *